United States Patent [19]
Unruh et al.

[11] Patent Number: 5,922,921
[45] Date of Patent: Jul. 13, 1999

[54] PROCESS FOR THE PRODUCTION OF N-BUTANOL

[75] Inventors: Jerry D. Unruh; Debra A. Ryan, both of Corpus Christi, Tex.; Shannon L. Dugan, Hutchinson, Kans.

[73] Assignee: Celanese International Corporation, Dallas, Tex.

[21] Appl. No.: 08/957,914

[22] Filed: Oct. 27, 1997

[51] Int. Cl.$^6$ ..................................................... C07C 29/14
[52] U.S. Cl. ............................................ 568/882; 568/881
[58] Field of Search ..................................... 568/840, 878, 568/880, 881, 884, 885, 882, 913

[56] References Cited

U.S. PATENT DOCUMENTS

| | | | |
|---|---|---|---|
| 4,263,449 | 4/1981 | Saito et al. ............................... | 560/263 |
| 4,826,799 | 5/1989 | Cheng et al. ............................ | 502/301 |

*Primary Examiner*—Michael L. Shippen
*Attorney, Agent, or Firm*—M. Susan Spiering

[57] ABSTRACT

Disclosed is the use of a Raney cobalt catalyst in the hydrogenation process for the production of n-butanol.

A process for the production of purified n-butanol comprising contacting in a hydrogenation zone n-butyraldehyde and hydrogen with an active porous cobalt catalyst under hydrogenation conditions of temperature and pressure for the production of alcohols from aldehydes, either in the substantial absence of water, or in the presence of water in an amount up to about 6 wt % based on the weight of the liquid hydrogenation reaction product to produce said reaction product comprising n-butanol, and purifying said reaction product by fractional distillation in the presence of about 0.01 to about 6 wt % of water, based on the total weight of feed to the fractionating column.

12 Claims, No Drawings

PROCESS FOR THE PRODUCTION OF N-BUTANOL

BACKGROUND OF THE INVENTION

1. Field of the Invention

This invention relates to an improved process for the production of a purified n-butanol by the hydrogenation of n-butyraldehyde and the fractional distillation of the resulting crude n-butanol.

2. Background Information Including a Description of Related Art

It is known to produce n-butanol by the hydrogenation of the n-butyraldehyde obtained, for example, by the hydroformylation of propylene by reaction with carbon monoxide and hydrogen. However, in order to be suitable for various applications, e.g., as a solvent for fats, waxes and resins, and in the manufacture of rayon, detergents and various butyl compounds, the n-butanol must have a high degree of purity including a specified low level of various impurities produced by the hydroformylation and hydrogenation reactions. To deal with this problem, the crude n-butanol produced by the hydrogenation reaction must be purified, generally by fractional distillation. One of the impurities intended to be removed by the distillation is di-n-butylether (DBE) which has an atmospheric boiling point of 142° C., but in the absence of water forms a binary azeotrope with n-butanol having an atmospheric boiling point of about 117.6° C. This is very close to the boiling point of pure n-butanol of about 117.2° C., making it difficult to separate DBE from n-butanol when water is not present. However in the presence of water, a ternary azeotrope of water, n-butanol and DBE is formed having a boiling point of about 90.6° C. which can be exploited in the separation of DBE from the bulk of the n-butanol product. Other impurities produced during the catalytic hydrogenation of n-butyraldehyde to form n-butanol are so-called "heavy ends," which are relatively high boiling and tend to break down during purification by distillation to form "permanganate time consumers" (PTC's), i.e., certain unsaturated compounds and chromophores such as olefins, aldehydes and ketones, during distillation. The PTC's, like other impurities such as DBE, may also produce an adverse effect on end use applications if present in the n-butanol product, and like DBE, their separation from the n-butanol product is facilitated by the presence of water in the distillation column.

When any of certain catalysts such as Raney nickel is used for the hydrogenation of n-butyraldehyde to n-butanol, a fairly large amount of water, e.g., about 8–15 weight percent (wt %), is added to the aldehyde feed both to decrease the amount of DBE otherwise formed as a side reaction of the hydrogenation of aldehyde in the absence of such amount of water, and to ensure that the bulk of the DBE which does form can be separated from the n-butanol product as the ternary azeotrope discussed previously, and that the removal of PTC's which form from the heavy ends in the fractionating column is also facilitated. However, the presence of such a large amount of water in the fractionating column results in a substantial expenditure of energy, generally through steam consumption, to vaporize the water present, and may also necessitate a larger column than would otherwise be necessary to carry out the purification. Thus, any change in the process is desirable which results in a decreased amount of water necessary in the reactor and the fractionating column and thus a reduction in energy consumption and possibly the size of the column, without any increase in the amount of DBE and PTC's present in the product.

The following prior art references may be considered material to the claimed invention.

U.S. Pat. No. 4,263,449, issued Apr. 21, 1981 to Saito et al., discloses a process for producing alcohols, e.g., butanol, by the hydroformylation of an alkenyl compound, e.g., propylene, and the hydrogenation of the resulting aldehyde in the presence of a hydrogenation catalyst, e.g., Raney cobalt. Water is added at a ratio of 0.5 to 30 times by weight based on the aldehyde produced by the hydroformylation before the hydrogenation.

U.S. Pat. No. 4,826,799, issued May 2, 1989 to Cheng et al., teach a process of making catalysts by the Raney process including the steps of pelletizing a Raney process metal alloy, e.g., of cobalt and aluminum, in a matrix of polymer and plasticizer followed by removal of plasticizer or plasticizer and polymer, and the leaching out of the aluminum with caustic. The catalyst may be used to hydrogenate an aldehyde to the corresponding alkanol, e.g., butanol.

SUMMARY OF THE INVENTION

In accordance with this invention, purified n-butanol is produced by a process comprising contacting in a hydrogenation zone n-butyraldehyde and hydrogen with an active porous cobalt catalyst under hydrogenation conditions of temperature and pressure for the production of alcohols from aldehydes, either in the substantial absence of water, or in the presence of water in an amount up to about 6 wt % based on the weight of the resulting crude n-butanol hydrogenation reaction product, and purifying the reaction product by fractional distillation in the presence of about 0.01 to about 6 wt % of water, based on the total weight of feed to the fractionating column.

The use of an active porous cobalt catalyst in the hydrogenation process surprisingly results in the production of significantly smaller amounts of most impurities, including DBE and heavy ends, than when a catalyst such as Raney nickel is employed. This allows for the use of a substantially lower amount of water in the fractionating column in which the n-butanol product from the hydrogenation process is purified, since less water is needed for the formation of the ternary azeotrope necessary to separate the DBE from the n-butanol, and the removal of the PTC's. This in turn reduces the energy, e.g., in the form of steam, necessary to vaporize the water in the column, and may also allow for the use of a smaller column, or higher production of n-butanol with an existing column.

DETAILED DESCRIPTION OF THE INVENTION

The n-butyraldehyde feed to the process of this invention may be obtained from any source, e.g., the noble metal-phosphine ligand catalyzed hydroformylation of propylene. If the feed is obtained from the latter process, it is not usually necessary to subject it to extensive purification before utilizing it in the hydrogenation, although such feed is generally treated to remove the phosphine ligand.

The active porous cobalt catalysts suitable for use in the hydrogenation reaction of this invention are prepared by treating an alloy of cobalt and at least one other metal, e.g., aluminum, with a chemical agent, e.g., sodium hydroxide, to extract the other metal from the alloy and obtain the cobalt in a highly porous form. Such active porous cobalt catalysts are known in the art as "Raney Cobalt" catalyst. They may be obtained commercially, e.g., from W. R. Grace & Co. and are typically listed under the "Raney" tradename. They may be unsupported or supported, for example, on a porous carrier such as alumina or silica, with the metallic portion containing, for example, at least about 80 wt % of cobalt, and any remaining metals being, for example, aluminum, iron, nickel and/or chromium, with chromium, if present, possibly acting as a promoter for the cobalt. For illustrative purposes only, the unsupported catalysts may have an average particle size of, for example, about 15 to about 60 microns, a specific gravity of, for example, about 6.5 to about 7.5, and a bulk density of, for example, about 14 to 18 lb/gal based on a catalyst slurry weight of 56% solids in water.

The hydrogenation is generally carried out under hydrogenation conditions for the production of alcohols from aldehydes, e.g., a temperature of about 100 to about 160° C., a hydrogen pressure of about 100 to about 700 psig, and a catalyst loading of about 2 to about 20 wt %, preferably about 8 to about 10 wt %, based on the weight of the liquid feed. In addition, the liquid feed should contain, for example, either substantially no water, or an amount of water, for example, up to about 6 wt %, preferably about 2 to about 6 wt %, and most preferably about 0.1 to about 3 wt %, based on the weight of crude hydrogenation reaction product. By "substantially no water" what is meant is no water is added to the reactor, and the reaction liquid contains only that water that is produced during the formation of butyraldehyde. The hydrogenation reaction may be carried out continuously, semi-continuously or batchwise, preferably with some backmixing during the reaction, e.g., a continuous slurry bed system operating between plug flow and backmixing. A rotating mixing element is not necessary, but if one is utilized, it may operate at a rotation rate of, for example, about 1000 to 2000 rpm. The residence time of the hydrogenation reactants in the reaction zone may be in the range, for example of about 10 to about 120 min. In many instances, the hydrogenation reaction product will contain no more than about 100 ppm of di-n-butylether (DBE) which is significantly less than the amount usually obtained when the hydrogenation is carried out with a Raney nickel catalyst, other conditions being equal.

As stated, the purification of the crude n-butanol from the hydrogenation zone is carried out by fractional distillation in the presence of about 0.01 to about 6 wt % of water, preferably about 0.1 to about 3 wt %, based on the weight of feed to the fractionating column. Since an amount of water within this range may not be present in the hydrogenation effluent, water may be added to such effluent before it is fed to the fractionator, if necessary to bring the level of water in the fractionating column up to the desired concentration. In this connection, it should be noted that water may act as a cooling agent within the column as well as being necessary to form the azeotrope necessary for the efficient separation of DBE, and to act as an agent for the removal of heavy ends. To achieve a cooling effect, most of the water is circulated within the column by either internal reflux wherein water vapor condenses toward the top of the column and flows back down to where it absorbs heat and is revaporized to start the cycle again, or external reflux wherein water-containing liquid streams, e. g., the ternary azeotrope or water-containing heavy ends discussed previously, are withdrawn from the column, most of the water in the stream is separated from the organics, e.g., by decantation, and the liquid water is returned to a point at the upper portion of the column.

The distillation is preferably carried out at atmospheric pressure, although it is possible to operate at subatmospheric or superatmospheric pressures, if desirable under certain circumstances.

In general, the number of trays in the column and amount of heat transferred to the material being purified in the column are sufficient to produce a liquid stream of purified n-butanol containing at least about 99.5 wt % of n-butanol. Typically, a liquid or vapor stream comprising n-butyraldehyde which has an atmospheric boiling point of 75.7° C. and, if the source of the n-butyraldehyde is the hydroformylation of propylene, about 9–10 wt % of isobutyraldehyde having an atmosphere boiling point of about 64° C., based on the total weight of aldehyde, is withdrawn at or near the top of the column; condensed ternary azeotrope of water, n-butanol and DBE containing essentially all of the DBE impurity in the hydrogenation effluent and having an atmospheric boiling point of about 90.6° C. is withdrawn in the upper portion of the column at a point below that of the n-butyraldehyde; and purified n-butanol having an atmospheric boiling point of about 117° C. is withdrawn at a point below that of the withdrawal of condensed ternary azeotrope. The remaining significant impurities, which are substantially higher boiling than n-butanol, are withdrawn as single compounds or mixtures at points below that of the purified n-butanol. Since the amounts of DBE impurity and most of the heavy ends in the hydrogenation effluent are substantially lower when an active porous cobalt catalyst is employed rather than a catalyst such as Raney nickel, all other conditions being equal, the amount of water which must be present in the column to form a ternary azeotrope containing substantially all of such DBE impurity and to remove the PTC's produced by the heavy ends is significantly reduced, resulting in a lower cost of energy to evaporate such water, and possibly higher production of n-butanol and/or a requirement for a smaller-sized column.

The following non-limiting examples further illustrate the invention.

EXAMPLE 1

In Example 1, a crude n-butyraldehyde stream obtained from the noble metal-phosphine ligand catalyzed hydroformylation of propylene and containing about 9–10 wt % of isobutyraldehyde based on the total weight of pure aldehydes in the stream, was hydrogenated using an unsupported active porous cobalt catalyst sold by the Grace Davison Division of W. R. Grace & Co., as "Raney Cobalt 2700" with a composition of at least 93.0 wt % cobalt and no more than 6.0 wt % aluminum, 0.7 wt % iron and 0.8 wt % nickel, an average particle size in the range of 20 to 50 microns, a specific gravity of about 7 and a bulk density of 15–17 lbs/gal based on a catalyst slurry weight of 56% solids in water. Prior to hydrogenation, the crude n-butyraldehyde was untreated except for removal of phosphine ligand utilized for the hydroformylation. The hydrogenation was carried out continuously in a stirred completely backmixed reactor at a temperature of 135–138° C., a hydrogen pressure of 400 psig and a stir rate of 1750 rpm. The catalyst loading was about 8–10 wt % based on the weight of the liquid reaction mixture in the reactor, the water content of the liquid hydrogenation effluent was controlled between 2.80 and 3.60 wt % based on the weight of crude n-butanol hydrogenation reaction product by the addition of water to the hydrogenation, and the flows to and from the reactor were controlled to provide a residence time in the reactor of close to 40 min.

Spot samples of crude hydrogenation reaction product were withdrawn after on-stream total process times of from 2 to 15 hours at intervals between withdrawal of samples of from about 1.2 to 3 hours, and analyzed for weight percent of water ($H_2O$) by Karl-Fischer titration and for parts per million of the following impurities by gas chromatography: n-butyraldehyde (n-BuH); di-n-butylether (DBE); butyl butyrates (BBt); butyl butyrals (BBl); butyric acids (BA); and the following heavy ends: Texanol (Tex) which is composed of trimers of esters of isobutyraldehyde; 2-ethyl-4-methylpentanediol (EMP); 2-ethylhexanol (EH); 2-ethyl-1,3-hexanediol (EHD); $C_{12}$trimer (C-12T) which is composed of trimers of esters of i-and n-butyraldehyde; and 2,2,4-trimethylpentanediol (TMP). Also assumed to be present in the crude hydrogenation reaction product were about 9–10 wt % of i-butyraldehyde based on the total weight of n- and i-butyraldehyde and about 9–10 wt % of i-butanol based on the total weight of n- and i-butanol.

were withdrawn and analyzed after total process times of between about 1.8 and 15 hours with intervals between withdrawals of samples of from about 0.5 to 3.2 hours.

The results of the analysis of impurities as the runs progress are shown in Table 1. The table also includes the feed rate to the hydrogenation reactor (Feed Rate=total feed rate of aldehyde), the product rate (Prod. Rate), i.e. effluent rate from the reactor, and the residence time (Res. Time) of reactants in the reactor, measured or calculated for the interval between samples.

TABLE 1

Comparative Examples of Raney Co versus Raney Ni catalyzed hydrogenation of crude butyraldehyde at 3–4 wt % water addition

| TIME* | EXAMPLE 1 | | | | | | | COMPARATIVE EXAMPLE A | | | | | |
|---|---|---|---|---|---|---|---|---|---|---|---|---|---|
| hours | 2 | 4.8 | 7 | 9 | 12 | 13.8 | 15 | 1.8 | 4.8 | 5.3 | 9.8 | 11.8 | 15 |
| $H_2O$ wt % | 2.80 | 3.00 | 3.40 | 3.50 | 3.50 | 3.60 | 3.30 | 4.00 | 4.40 | 3.50 | 3.80 | 3.80 | 3.90 |
| n-BuH ppm | 566 | 718 | 552 | 591 | 505 | 531 | 678 | 547 | 564 | 300 | 307 | 591 | 893 |
| DBE ppm | 41 | 42 | 40 | 40 | 46 | 43 | 46 | 96 | 114 | 185 | 254 | 482 | 517 |
| BBt ppm | 75 | 66 | 46 | 60 | 51 | 43 | 46 | 62 | 68 | 52 | 81 | 110 | 113 |
| BBl ppm | 98 | 110 | 90 | 100 | 94 | 86 | 94 | 89 | 70 | 148 | 252 | 284 | 310 |
| BA ppm | 2276 | 1189 | 938 | 1714 | 1124 | 933 | 1273 | 467 | 1058 | 104 | 710 | 417 | 545 |
| Tex ppm | 34 | 18 | 15 | 21 | 19 | 45 | 50 | 17 | 18 | 14 | 68 | 138 | 153 |
| EMP ppm | 41 | 84 | 90 | 87 | 89 | 86 | 92 | 35 | 36 | 86 | 188 | 186 | 54 |
| EH ppm | 1109 | 1052 | 1035 | 1107 | 1102 | 1058 | 1071 | 987 | 996 | 995 | 2919 | 4501 | 4502 |
| EHD ppm | 85 | 115 | 108 | 114 | 240 | 187 | 257 | 186 | 206 | 137 | 177 | 257 | 313 |
| C-12T ppm | 200 | 150 | 171 | 170 | 0 | 110 | 0 | 0 | 0 | 0 | 344 | 625 | 1479 |
| TMP ppm | 23 | 39 | 35 | 22 | 39 | 106 | 97 | 29 | 43 | 27 | 53 | 2 | 10 |
| Feed Rate g/min | | 21.5 | | 20.9 | | 20.2 | 21.3 | | 21.1 | | 19.3 | | 20.3 |
| Prod. Rate g/min | | 22.3 | | 24.1 | | 27.3 | 24.3 | | 21.3 | | 20.0 | | 18.6 |
| Res. Time min | | 38.1 | | 39.1 | | 40.5 | 38.4 | | 38.8 | | 42.4 | | 40.3 |

*Time is from the start of the process.

COMPARATIVE EXAMPLE A

In Comparative Example A, the procedure of Example 1 was generally followed except that the hydrogenation catalyst was a Raney nickel sold by the Grace Davison Division of W. R. Grace & Co. as "Raney Nickel 3300", i.e. an unsupported molybdenum-promoted porous nickel in which the metallic component comprised about 90.0–99.1 wt % of nickel, about 0.5–1.5 wt % of molybdenum, no more than about 8.0 wt % of aluminum, and no more than about 0.8 wt % of iron, and having an average particle size of about 25 to about 65 microns, a specific gravity of about 7, and a bulk density of about 15–17 lbs/gal. based on a catalyst slurry weight of 56% solids in water; the water content was controlled to between 3.50 and 4.40 wt % based on the weight of the crude n-butanol hydrogenation reaction product; and the spot samples of hydrogenation reaction product As shown in the values of Table 1, the process of Example 1 under the invention, utilizing an active porous cobalt hydrogenation catalyst (Raney Cobalt), yielded a crude hydrogenation reaction product containing much less di-n-butylether (DBE) and, particularly as the total reaction time approached 15 hours, a much smaller quantity of heavy ends, than the process of Comparative Example A which employed a conventional Raney nickel hydrogenation catalyst. In view of this, the hydrogenation product of Example 1, when purified in a fractionating column, requires a relatively small amount of water, i.e., no more than about 6 wt % based on the weight of feed to the column to form an amount of ternary azeotrope of water, n-butanol and DBE sufficient to remove substantially all the DBE in the hydrogenation reaction product, and also sufficient to remove the PTC's. In contrast, the hydrogenation product of Comparative Example A, in view of its much higher content of DBE and heavy ends, requires a significantly larger amount of water in the fractionating column, e.g., above about 8 wt %, to remove substantially all of the DBE, and PTC's produced in the column. Alternatively, the amount of DBE and heavy ends produced in the hydrogenation reaction when a conventional Raney nickel catalyst is employed, as shown in the results of Comparative Example A, can be reduced by adding a greater amount of water, e.g., at least about 8 wt %, to the liquid hydrogenation reaction mixture. However, the amounts of these impurities produced when the larger amounts of water are used is still generally greater than when an active porous cobalt hydrogenation catalyst is employed with a substantially smaller amount of water in the hydrogenation reactor. Furthermore, most of any water added to the Raney nickel catalyzed hydrogenation to reduce the formation of impurities is ultimately transferred to the fractionating column when the crude n-butanol hydrogenation product is purified. Thus, a larger amount of water is inevitably present in the fractionating column when Raney nickel is employed than when active porous cobalt catalyst (Raney Cobalt) is employed. The use of the latter catalyst under the invention therefore results in a lower energy cost and higher production of n-butanol and/or the necessity for a smaller column. This being due to the requirement for less water in the column to achieve the desired degree of purification than when a conventional Raney nickel hydrogenation catalyst is employed.

EXAMPLE 2

The procedure of Example 1 was followed except that no additional water was added to the hydrogenation reaction, the effluent from which therefore contained only the water, if any, present in the propylene hydroformylation effluent and/or formed in the hydrogenation reaction; and the process was continued for over 200 hours. Table 2 shows the results of the analyses of samples withdrawn at approximate 20 hour intervals as well as the hydrogenation feed rate, product rate and residence time at the time of each sample withdrawal.

TABLE 2

Comparative example of use of Raney Co catalyzed hydrogenation of crude butyraldehyde with no additional water added to the reaction

| TIME* hours | 5 | 19 | 41 | 63 | 80 | 92 | 121 | 141 | 162 | 184 | 200 |
|---|---|---|---|---|---|---|---|---|---|---|---|
| $H_2O$ wt % | 0.140 | 0.000 | 0.010 | 0.002 | 0.002 | 0.005 | 0.191 | 0.127 | 0.004 | 0.008 | 0.097 |
| n-BuH ppm | 713 | 528 | 600 | 4439 | 1103 | 626 | 1289 | 1789 | 2008 | 2275 | 2175 |
| DBE ppm | 25 | 28 | 31 | 40 | 27 | 31 | 33 | 34 | 37 | 40 | 41 |
| BBt ppm | 37 | 42 | 46 | 75 | 47 | 51 | 56 | 62 | 67 | 73 | 70 |
| BBl ppm | 233 | 252 | 289 | 825 | 304 | 394 | 426 | 442 | 570 | 658 | 683 |
| BA ppm | 721 | 373 | 443 | 1539 | 505 | 766 | 958 | 1018 | 1151 | 1741 | 1475 |
| Tex ppm | 6 | 6.1 | 9 | 1 | 8 | 8 | 6 | 7 | 8 | 4 | 7 |
| EMP ppm | 24 | 22 | 21 | 23 | 22 | 23 | 31 | 22 | 26 | 22 | 22 |
| EH ppm | 81 | 73 | 75 | 79 | 75 | 76 | 87 | 77 | 66 | 92 | 83 |
| EHD ppm | 190 | 102 | 118 | 155 | 126 | 128 | 213 | 182 | 192 | 244 | 254 |
| C-12T ppm | 39 | 16 | 23 | 14 | 26 | 26 | 43 | 17 | 40 | 7 | 13 |
| TMP ppm | 27 | 22 | 23 | 35 | 20 | 22 | 0 | 22 | 21 | 28 | 22 |
| Feed Rate g/min | 21.4 | 22.1 | 20.0 | 20.0 | 26.2 | 20.3 | 20.3 | 20.2 | 19.6 | 20.0 | 20.6 |
| Prod. Rate g/min | 21.5 | 22.7 | 20.4 | 20.2 | 20.6 | 21.8 | 20.4 | 20.7 | 20.0 | 20.8 | 20.8 |
| Res. Time min | 36.9 | 35.0 | 38.9 | 39.3 | 38.6 | 36.4 | 38.9 | 38.4 | 39.7 | 38.2 | 38.2 |

*Time is from the start of the process.

Comparison of the results of Examples 1 and 2 as shown in Tables 1 and 2 indicate that when no additional water is added to the hydrogenation reaction, as in Example 2, even smaller amounts of DBE and such heavy ends as Texanol, 2-ethyl-4-methylpentanediol, 2-ethylhexanol and $C_{12}$ trimer, are formed than when additional water is added to the hydrogenation reaction as in Example 1. Thus, when no additional water is added to the hydrogenation reactor, even less water is required in the fractionating column to remove the DBE by formation of the ternary azeotrope as described previously, and the PTC's produced from the heavy ends present in the column. An even greater savings can therefore be achieved due to a lower energy requirement for the vaporization of water in the column.

We claim:

1. A process for the production of purified n-butanol comprising contacting in a hydrogenation zone n-butyraldehyde and hydrogen with an active porous cobalt catalyst under hydrogenation conditions of temperature and pressure for the production of alcohols from aldehydes, either in the substantial absence of water, or in the presence of water in an amount up to about 6 wt % based on the weight of the liquid hydrogenation reaction product to produce said reaction product comprising n-butanol, and purifying said reaction product by fractional distillation in the presence of about 0.01 to about 6 wt % of water, based on the total weight of feed to the fractionating column.

2. The process of claim 1 wherein said hydrogenation reaction product comprises no more than about 100 ppm of di-n-butylether.

3. The process of claim 1 wherein said n-butyraldehyde is obtained from the hydroformylation of propylene.

4. The process of claim 1 wherein the metallic portion of said active porous cobalt catalyst contains at least about 80 wt % of cobalt.

5. The process of claim 4 wherein said catalyst is prepared by treating an alloy of cobalt and at least one other metal with a chemical agent to extract the other metal from the alloy and obtain the cobalt in a highly porous form.

6. The process of claim 5 wherein said other metal is aluminum and said treating agent is sodium hydroxide.

7. The process of claim 5 wherein said catalyst is unsupported and has a particle size of about 15 to about 60 microns, a specific gravity of about 6.5 to about 7.5, and a bulk density of about 14, to 18 lb/gal based on a catalyst slurry weight of about 56% solids in water.

8. The process of claim 1 wherein said hydrogenation is carried out continuously with at least some with backmixing at a temperature of about 100 to about 160° C., a hydrogen pressure of about 100 to about 700 psig., and a catalyst loading of about 2 to about 20 wt %, based on the weight of the liquid feed.

9. The process of claim 1 wherein said fractional distillation is carried out such that a condensed ternary azeotrope of water, n-butanol and di-n-butylether (DBE) containing substantially all the DBE in the hydrogenation effluent is withdrawn at the upper portion of the column, purified n-butanol is withdrawn at a point below that of said azeotrope, and the higher boiling impurities are withdrawn at points below that of the withdrawal of said purified n-butanol.

10. The process of claim 9 wherein said purified n-butanol contains at least about 99.5 wt. % of pure-n-butanol.

11. A process for the production of purified n-butanol comprising contacting in a hydrogenation zone n-butyraldehyde and hydrogen with an active porous cobalt catalyst under hydrogenation conditions of temperature and pressure for the production of alcohols from aldehydes in the substantial absence of water to produce n-butanol, and purifying said n-butanol by fractional distillation in the presence of about 0.01 to about 6 wt % of water, based on the total weight of feed to the fractionating column.

12. A process for the production of purified n-butanol comprising contacting in a hydrogenation zone n-butyraldehyde and hydrogen with an active porous cobalt catalyst under hydrogenation conditions of temperature and pressure for the production of alcohols from aldehydes in the presence of water in an amount up to about 6 wt % based on the weight of the liquid hydrogenation reaction product to produce n-butanol, and purifying said n-butanol by fractional distillation in the presence of about 0.01 to about 6 wt % of water, based on the total weight of feed to the fractionating column.

* * * * *